United States Patent [19]

Farrar et al.

[11] 4,244,375
[45] Jan. 13, 1981

[54] TRANSCUTANEOUS ELECTRODE WITH FINGER OPERATIVE ATTACHMENT ASSEMBLY

[75] Inventors: Alfred O. Farrar, Cranbury; Howard M. Hochberg, East Windsor; Flave L. Jones, Lincroft, all of N.J.

[73] Assignee: Hoffmann-La Roche Inc., Nutley, N.J.

[21] Appl. No.: 9,902

[22] Filed: Feb. 7, 1979

Related U.S. Application Data

[63] Continuation of Ser. No. 801,691, May 31, 1977, abandoned.

[51] Int. Cl.$^3$ .............................................. A61B 5/04
[52] U.S. Cl. ............................................................. 128/642
[58] Field of Search .............. 128/642, 784, 785, 788, 128/215, 218 D, 321, 346; 81/321-323; 269/254 R, 229

[56] References Cited

U.S. PATENT DOCUMENTS

| | | | |
|---|---|---|---|
| Re. 28,990 | 10/1976 | Hon et al. | 128/642 |
| 2,082,782 | 6/1937 | Allen | 128/321 X |
| 3,055,364 | 9/1962 | Myerson et al. | 128/218 D X |
| 3,144,178 | 8/1964 | Sarnoff | 128/218 D X |
| 3,354,881 | 11/1967 | Bloch | 128/215 |
| 3,580,242 | 5/1971 | La Croix | 128/642 |
| 3,750,650 | 8/1973 | Ruttgers | 128/642 |
| 4,000,745 | 1/1977 | Goldberg | 128/785 |
| 4,010,758 | 3/1977 | Rockland et al. | 128/785 |
| 4,058,128 | 11/1977 | Frank et al. | 128/785 |

FOREIGN PATENT DOCUMENTS

| | | | |
|---|---|---|---|
| 7419264 | 9/1974 | Fed. Rep. of Germany | 128/642 |
| 2235666 | 1/1975 | France | 128/642 |
| 2247263 | 5/1975 | France | 128/785 |

OTHER PUBLICATIONS

Junge, "Einmel-Elektrode . . . ", George Hase & Suhn Feinwerktechnik, 1973.
Parker et al., "Tungsten Ball Microelectrode . . . ," EEG & Clin. Nevra, vol. 35, No. 6, pp. 647-651, Dec. 1973.
Hon, "Inst. of Fetal Heart Rate . . . ", Obs. & Gyn., vol. 30, No. 2, Aug. 1967, pp. 281-286.

*Primary Examiner*—Lee S. Cohen
*Attorney, Agent, or Firm*—Jon S. Saxe; Bernard S. Leon; Mark L. Hopkins

[57] ABSTRACT

A disposable electrode for direct transcutaneous derivation of patient biopotentials, such as the ECG of an unborn fetus, the active electrode element of which has a tuberous pin configuration with at least one tuberosity arranged along its length for enabling atraumatic attachment to and removal from the patient. The active electrode element may be of curved and multi-tuberous configuration for particularly facilitating application and firm attachment thereof substantially parallel to the skin surface. Several embodiments of disposable applicator are disclosed by which the sense of feel of the effort of and during application is retained. These include a flexible member elongated for easy grasping by the hand and having one end thereof designed to cooperatively engage the electrode for stability yet permit the physician's finger(s) to remain in contact with the electrode and a locking applicator arrangement which includes a displaceable locking piece enabling the electrode to firmly remain upon the applicator as the former is administered to the patient.

27 Claims, 20 Drawing Figures

TRANSCUTANEOUS ELECTRODE WITH FINGER OPERATIVE ATTACHMENT ASSEMBLY

This is a continuation, of application Ser. No. 801,691 filed May 31, 1977, now abandoned.

BACKGROUND OF THE INVENTION

Transcutaneous electrodes are used for long term monitoring of electro-physiological phenomenon because they are easily retained for long periods, provide a good signal, and are amenable to attachment to difficult areas. One of the more common uses is for detecting the fetal electrocardiogram (ECG) and other heart beat signals during labor, where an electrode must be placed easily, remain firmly attached, and be atraumatic, especially on removal.

The prior art teaches the use of several types of electrodes for transcutaneous monitoring, including standard injection needles, practically all of which are administered to the patient substantially perpendicular to the skin, thus risking the danger of too deep a puncture, etc. To facilitate holding the transcutaneous electrode in place, especially in fetal monitoring, several adaptations have been proposed and/or used, including the surgical clip arrangement of Hon (Instrumentation of Fetal Heart Rate and Fetal Electrocardiography III. Fetal ECG Electrodes: Further Observations, Obstet. Gyn. 30:281,1967); the fish-hook type arrangement of La Croix (U.S. Pat. No. 3,580,242); the double and single spiral arrangements of Ruttgers and Hon (U.S. Pat. No. 3,750,650 and RE 28,990 respectively); and the barbed, straight needle arrangement of Junge (German Patent Application No. 74,19264).

The surgical clip and spiral electrodes are traumatic (the latter primarily from the torque created on application and must be inserted (and in the case of the surgical clip also removed) with a special tool, placing the surgeon's hand well away from the presenting part, and thus losing the "feel" of the situation, reducing physician confidence, and adding a possibility for error in placement. Since the physician is trained to palpate (i.e. feel) and use this modality to a great extent, this loss can be rather disconcerting.

The fish-hook electrode is also traumatic, especially on removal. The barbed needle electrode is significantly smaller than the others and offers a better opportunity for "feel", but its rough edges, i.e. the multiplicity of little barbs, also tend to cause trauma. Moreover, application thereof is difficult in the absence of an applicator tool, with the electrode often slipping away from the entry site when force is applied to effect skin penetration.

SUMMARY OF THE INVENTION

It is, therefore, a principle objective of this invention to provide a transcutaneous electrode arrangement which overcomes the aforementioned drawbacks of the prior art arrangements, i.e. a transcutaneous electrode arrangement which is small, atraumatic and easily placed, in particular substantially parallel to the skin surface, while retaining the "feel" of the situation, and remaining firmly attached, yet is able to be conveniently and easily removed when desired.

In accordance with the invention there is provided an electrode arrangement for direct transcutaneous derivation of patient biological parameters, such as the ECG of an unborn fetus with the improvement comprising the active electrode element having a tuberous pin configuration with at least one tuberosity arranged along the length thereof for enabling atraumatic attachment and removal of the electrode to respectively from the patient.

There are disclosed herein electrode/applicator combinations which allow relatively atraumatic transcutaneous insertion while retaining a sense of "feel" of the effort; and, an electrode similarly atraumatic on removal, and not critical to the form of removal. In contrast, it is well known, as example, that the spiral electrodes must be carefully unscrewed and the skin clip carefully separated to prevent severe trauma. As may be expected, too, trauma caused by the barbed arrangements can hardly be avoided.

The transcutaneous electrode of the present invention is comprised of a means to insert a metal or other electrically conductive substance into the skin, substantially parallel to the skin surface. This is comprised of an appropriately rigid, pointed stem or pin having a tuberosity (i.e. a rounded prominence) or preferably multiple tuberosities to hold it in place. The skin tension will prevent easy backward displacement by closing around the tuberosities, but the non-barbed, non-pinching nature thereof allows easy, atraumatic insertion and removal.

This active electrode element extends from a base member which also has mounted thereto a reference electrode element (indifferent plate). This latter element may be situated, for example, on a portion of the base opposing the active element to complete the bipolar arrangement.

In at least one electrode embodiment herein described, the stem or pin electrode element may be bent, thus giving rise to a curved form of transcutaneous electrode which can provide even better "feel" and easier insertion.

Various insertion means (i.e. applicators) are provided which allow the desired sense of "feel". Such may, for example, take the form of a relatively flexible elongated member resembling an open-ended wrench. The electrode is received into a notched and bevelled end thereof and is held firmly in place, not only by the cooperative design of the electrode body and the engaging end of the applicator, but also by drawing and holding the connector wire(s) leading to the electrode tight against the shaft of the member and/or by securing the wire(s) in a fork-like notch provided at the opposite end thereof. The tips of the physician's fingers are used to guide the member, and the flexibility thereof promotes the much desired sense of "feel". Most importantly perhaps is the fact that the applicator enables the electrode to be stably maintained during application of the patient, while allowing the physician's finger tip(s) to make direct contact with the electrode body during as well as prior to application. The electrode is intended preferably to be inserted so that the pin or stem constituting the active electrode element lies substantially parallel to the patient's skin surface. This orientation of insertion can be facilitated by the above-mentioned curved-stem electrode which resembles a surgical needle.

In another applicator embodiment, the tuberous stem or pin electrode is held in a finger tip flexible mold, having an orifice therein through which the electrode protrudes. The orifice is dimensioned to enable the electrode to be held in place firmly by the finger by easy placement, and yet allow the electrode to be easily released once engagement with the patient has taken place.

An especially preferred embodiment of applicator disclosed herein involves a locking arrangement on an elongated cylindrical or flat main member, in which the electrode is received at the one end of the applicator and locked thereon by a slidable or rotatable locking part, there to be securely retained until release is desired, which is effected by moving the locking part to a retracting position.

An arrangement for maintaining electrode sterility prior to actual application to the patient is also disclosed, which comprises a cover or canopy made of, for example, light sterile latex, which surrounds the tuberous active electrode element until the moment the electrode is applied. By placing the electrode arrangement against the tissue and applying pressure the cover and then the tissue is punctured, providing protection from contamination of the engaging electrode element up to the moment of actual puncture of the skin at the desired site, and limiting contamination only to the actual site of puncture.

BRIEF DESCRIPTION OF THE DRAWINGS

The above-mentioned and other objects and features of this invention will become more apparent with reference to the following detailed description taken in conjunction with the accompanying drawings in which.

DESCRIPTION OF THE PREFERRED EMBODIMENT(S)

With reference to the Figures, it is pointed out that the illustrations are not necessarily drawn to scale, but rather are exaggerated somewhat for ease of illustration and understanding.

Figure 1:
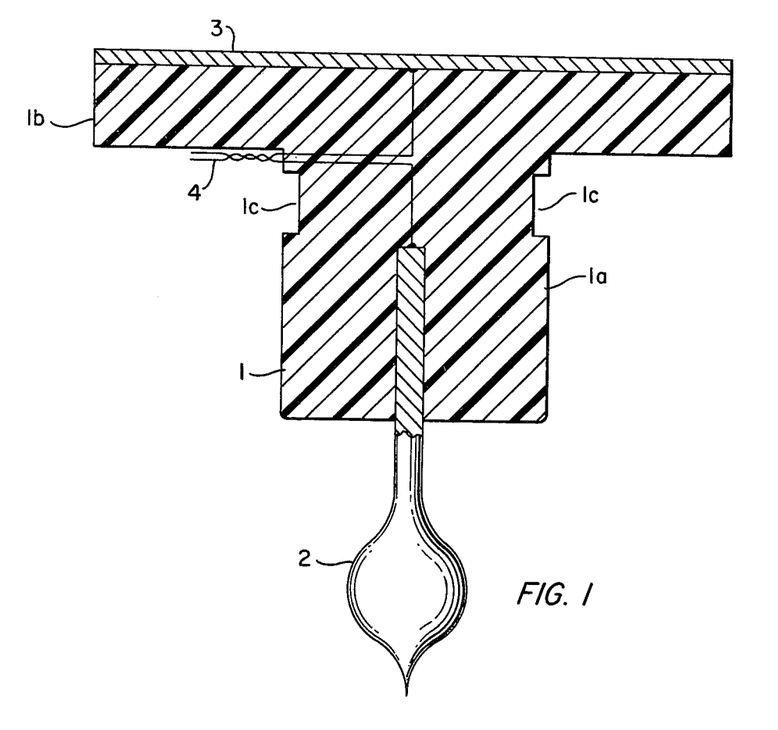
FIG. 1 illustrates in an enlarged sectional side view a first electrode according to the invention, employing an active electrode element having a single tuberosity.

Referring to FIG. 1, there is illustrated in an enlarged sectional side view a first embodiment of electrode for the direct transcutaneous derivation of biopotentials, such as the ECG of an unborn fetus. The depicted electrode is comprised of a base 1 of electrically insulating material such as nylon, a pin-like but tuberous active electrode element 2 and a reference electrode element (indifferent plate) 3. A pair of electrical leads 4 completes the electrode, which leads are connected to the active and reference electrode elements respectively.

The base 1 has at least a first portion 1a, preferably of substantially cylindrical shape, and may, as indicated in FIG. 1, have a second portion 1b located atop the cylindrical portion 1a and preferably integral therewith, which top portion is preferably also of substantially cylindrical shape and coaxial with base portion 1a, but possessing a larger cross-sectional diameter.

The pin-like active electrode element 2 illustrated in FIG. 1 protrudes from the end of cylindrical base portion 1a and has at least a single exposed tuberosity along the length thereof, in this case proximate the free end. Active electrode element 2 is here depicted in a straight configuration and having a pointed free end. Active element 2 is arranged to extend from the lower end of cylindrical base portion 1a substantially along the longitudinal axis of the latter. The lead 4 to active element 2 makes contact at the embedded end of the latter safely within the interior of the base 1.

The actual dimension and curvature of the tuberosity(s) of active element 2 are based upon the ability of the interior tissue tension to assist in retaining the electrode following application, tempered, however, by the desire of requiring only a small application force to administer the electrode to the patient.

Figures 2A, 2B:
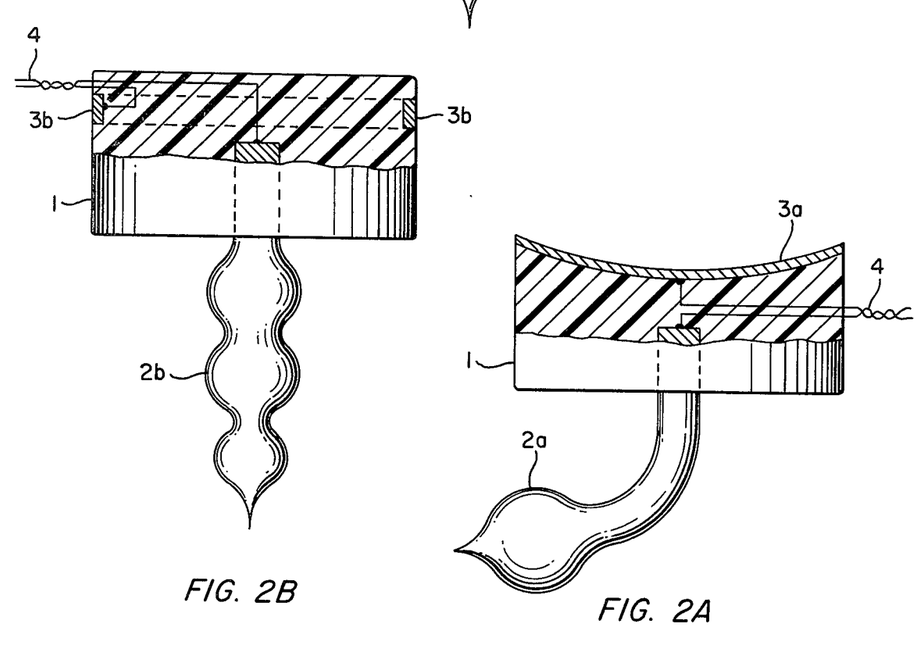
FIG. 2A illustrates in an enlarged, breakaway, partially sectional side view another embodiment of electrode according to the invention, in which the single-tuberosity active electrode element is bent or curved to facilitate the application thereof to the patient.
FIG. 2B illustrates in an enlarged, breakaway, partially sectional side view yet another embodiment of electrode according to the invention, employing an active electrode element having, however, multiple tuberosities.

Active element 2 may, in place of the straight pin-like configuration depicted in FIG. 1, take on a curve form, such as that shown in FIG. 2A, in which the active element, while at least initially projecting outward from the base substantially along the longitudinal axis of cylindrical base portion 1a, has its free end arranged to form an angle relative to the initially projecting portion thereof (i.e. at the point it breaks surface with the base 1) of less than 180° and preferably in the vicinity of 90°, although the precise angle is not critical. The curvature of the active element 2 facilitates application of the electrode to the patient in the preferred orientation in which the active element is inserted into the patient's skin substantially parallel to the skin surface.

Figure 2C:
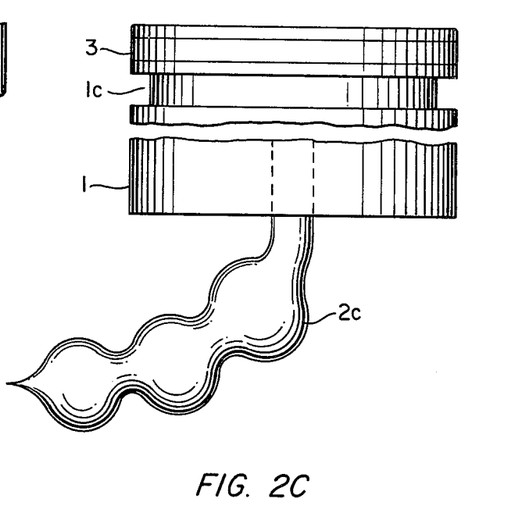
FIG. 2C illustrates in an enlarged breakaway side view still another embodiment of electrode according to the invention, employing the multiple tuberosity active electrode element of FIG. 2B in a curved configuration similar to that of FIG. 2A.
Figure 2D:
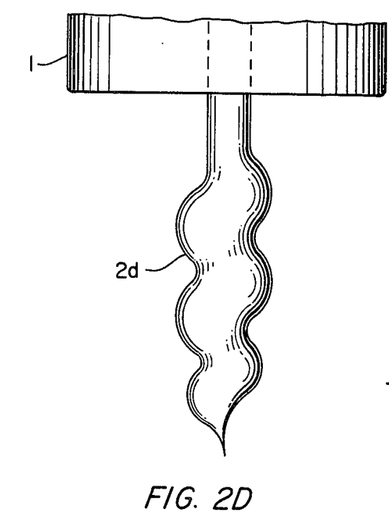
FIG. 2D illustrates in an enlarged breakaway side view, another embodiment of electrode according to the invention, in which the active electrode element has a smooth-threaded, screw-like configuration.

Also, active element 2 preferably may, in lieu of the single-tuberosity configuration depicted in FIGS. 1 and 2A, be provided along its exposed portion, either in actuality or effectively, with multiple tuberosities, such as are illustrated in FIGS. 2B, 2C and 2D.

FIG. 2B in particular illustrates a multiple-tuberosity, straight-pin configuration 2b, in which the first tuberosity is located proximate the pointed free end of active element 2b and the final tuberosity is spaced somewhat from the surface of the base portion of 1a bearing the active electrode element. The various tuberosities define largely symmetrical, smooth indentations therebetween which facilitates maintaining the attached electrode in place following application, and yet such an active electrode element design enables relatively easy atraumatic removal when desired.

While the actual size and curvature of the individual tuberosities are predetermined in dependence on the internal tissue tension, for ease of application the tuberosity located proximate the free end may be somewhat similar in size then the others. Moreover, the tuberosities may continue to increase in size away from the free end of active element 2, and thereby define as a result an ever-increasing force needed for additional penetration into the patient's tissue.

FIG. 2C illustrates in particular the preferred curved-pin configuration of FIG. 2A with multiple tuberosities such as that shown in FIG. 2B. This combination provides in one and the same electrode the advantages regarding insertion and placement thereof associated to the FIG. 2A configuration with the atraumatic placement-retaining advantages of the FIG. 2B configuration.

FIG. 2D illustrates what may be described as at least one substantially continuous tuberosity or a series of tuberosities forming a more or less continuous, smooth, thread-like (helical) configuration along the shaft 2d, which also has a pointed free-end. Such an arrangement possesses the placement-retaining capability of say the configuration according to FIG. 2B and provides in addition thereto the capability of being screwed into or out of the epidermus of the patient, as and if desired, to further reduce the possibility of any trauma, as well as providing a convenient means for governing the extent of penetration into the patient's tissue. It is to be understood that the active electrode element 2d of FIG. 2D may also take on a curved configuration similar to that of FIG. 2C, and thereby retain the above-indicated advantages in combination with the earlier-mentioned advantages of a curved configuration.

FIGS. 1, 2A and 2B illustrate further that the reference electrode element 3 may be configured and located on base 1 in various different embodiments, and may in connection therewith take the form of a film or band of electrically conductive material or instead a plate or disc. For example, in FIG. 1, reference element 3 is shown in the form of a thin plate or disc-like configuration situated atop the top flat portion 1b of the base. The lead 4 associated to the reference electrode 3 is connected to the latter on the underside thereof, preferably near the center region. FIG. 2A, on the other hand, shows a base portion 1a without top portion 1b, in which the top surface of cylindrical base portion 1a is concave, in order to facilitate the fit of the electrode with the fingertip of the person administering the electrode to the patient. The reference electrode element 3a, as shown, covers this concave surface.

Looking to FIG. 2B, there is again depicted a base 1 arrangement comprised of only the cylindrical first portion 1a. However, in this instance reference electrode element 3, rather than being mounted on the end of the cylindrical base portion 1a or 1b opposite the active element 2, instead takes the form of a ring configuration 3b mounted around the circumference of cylindrical base portion 1a so as to have its operative surface preferably flush with the side of the base. In such a configuration, the associated electrical lead 4 may be connected on the inside ring surface of element 3b.

In general, the relative size of the electrode embodiments depicted herein are on the order of or smaller than the aforementioned Junge electrode, preferably less than 5 mm in length for the active electrode element and 2–3 mm in cylindrical length for the base.

In all cases, active and reference electrode elements 2 and 3 are metallic or otherwise electrically conductive and mutually insulated from one another by the base material.

Various arrangements of the electrical leads 4 are depicted in FIGS. 1, 2A and 2B which primarily accommodate the design and structure of the base 1. While the illustrated arrangements are considered preferred configurations, it is to be understood that other suitable and convenient lead arrangements are within the scope of this invention.

More particularly, the electrical lead configuration of FIG. 1 is intended to facilitate the application of the patient of the electrode depicted with the electrode applicator illustrated in FIGS. 3A and 3B, as will be more particularly discussed hereinafter. In this configuration of FIG. 1, it is to be noted that not only do the leads make electrical contact with the active and reference electrode elements well within the interior of the base material, but that the leads run through the base interior to exit proximate the junction of first cylindrical base portion 1a and top base portion 1b.

FIGS. 2A and 2B also show the leads 4 to be exiting from the side of the base 1 and make electrical contact with the active and reference electrode elements well within the interior of the base material. FIG. 2B in particular illustrates the reference electrode lead making contact with the cylindrical reference element 3b on the inside surface thereof.

Figure 3A:
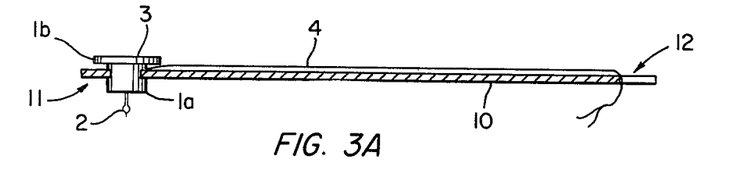
FIGS. 3A-3B show respectively in a cross-sectional side and a top view a first embodiment of electrode applicator, taking the form of an elongated, flexible member resembling an open-ended wrench, with the electrode of FIG. 1 received thereon and ready for application.
Figure 3B:
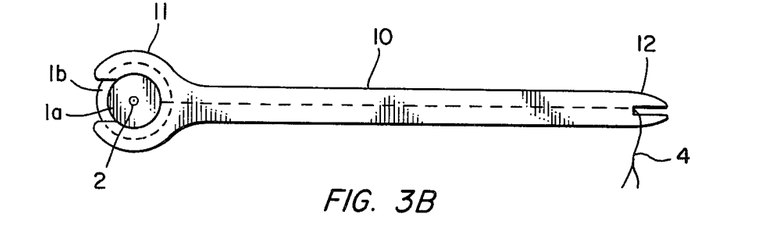

FIGS. 3A and 3B illustrate respectively in side section and top views a first embodiment of finger-operable applicator for use, in particular, in connection with the electrode embodiment depicted in FIG. 1. The applicator of FIGS. 3A and 3B is a flexible, elongated member 10 having the appearance of an open-ended wrench, with a fork-shaped first end 11 constituting the electrode receiving end and the other end 12, also fork-shaped, employed as the electrode wire or lead receiving end. The electrode receiving end 11 is comprised of a pair of relatively thick, blunted tines which define a space therebetween dimensioned to closely cooperate with the cross-sectional diameter of the electrode cylindrical base portion 1a. The wire-receiving end 12 of applicator 10 has, on the other end, a pair of slender and somewhat rounded tines which define a substantially parallel-walled narrow channel having a width dimension intended to closely cooperate with the cross-sectional dimension of the electrode lead(s) 4.

FIGS. 3A and 3B show the electrode of FIG. 1 properly received unto the elongated member 10 and stabilized for ready application to the patient's skin. The illustrated straight-pin, single-tuberosity electrode projects in a direction substantially perpendicular to the longitudinal direction of the applicator. The electrical lead(s) extend along the length of the applicator to be tucked into the slit at the wire receiving end 12, there to be pulled taut, if desired, by the physician prior to application and permitting a proper amount of tension to remain exerted upon the electrode lead(s) in order to facilitate the electrode being securely held in place within the channel of the electrode receiving end 11. The tautness of the lead(s) can be maintained merely by the physician's grasp of the applicator during the approach to and application of the electrode into the patient's tissue.

Figure 4:
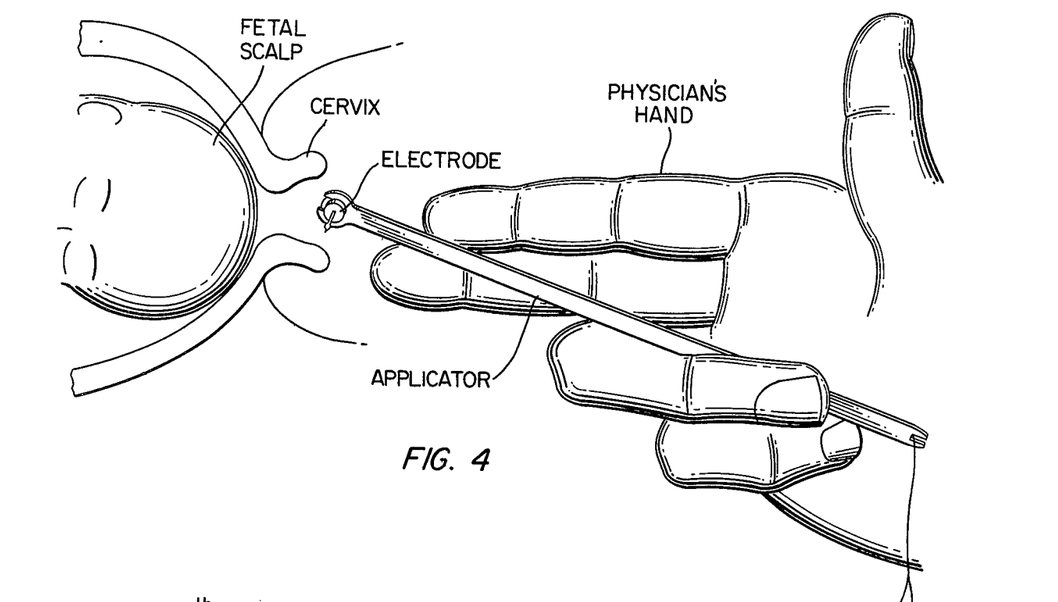
FIG. 4 illustrates the electrode/applicator arrangement of FIGS. 3A and 3B about to be applied by the physician's hand to the fetal scalp at the opening of the cervix.

FIG. 4 illustrates the electrode arrangement of FIGS. 3A and 3B as the electrode is about to be applied by the physician to the fetal scalp at the opening of the cervix, as is apparent. The elongated structure of applicator 10 conveniently cooperates with the extended forefinger of the physician's hand, wherein the wire receiving end 11, and therefore the lead(s), are firmly clasped between the thumb, the palm and other fingers. Such an arrangement provides to the physician the necessary stability of the electrode during placement as well as permits the physician the desired direct feel of the situation, thus maintaining physician confidence particularly in applications of the electrode involving difficult circumstances, such as are depicted in FIG. 5 in reaching the unborn fetus as early as possible during the birth process.

The base structure 1 of the electrode may be further adapted to facilitate cooperative engagement with the applicator of FIGS. 3A and 3B. In this regard, reference is made to FIG. 1 in which there is provided in the base a pair of oppositely-disposed, transversely-running grooves 1c having a cross-sectional dimension approximating the thickness of the elongated applicator 10. Such an engaging arrangement further enables the electrode to be securely maintained in position during the approach to and application into the intended tissue area of the patient. The grooves 1c may also be continued fully around the base to form a concentric groove about base portion 1a. Such is illustrated for example by the groove 1c in the base of the electrode depicted in FIG. 2C.

Alternatively, the cylindrical base portion 1a may be provided with a pair of oppositely-disposed, longitudinally-running flat sides for engagement with the applicator of FIGS. 3A and 3B. Such would provide a precise orientation of the electrode, as would, of course, be the case also with the oppositely-disposed grooves 1c of FIG. 1. A precise orientation would be desirable in regard to the possible asymmetrical aspects of the electrode, in particular the point of exit of the leads from the base portion and even more particularly with regard to the active electrode element having the curved electrode configuration depicted in FIGS. 2A and 2C.

Figure 5:
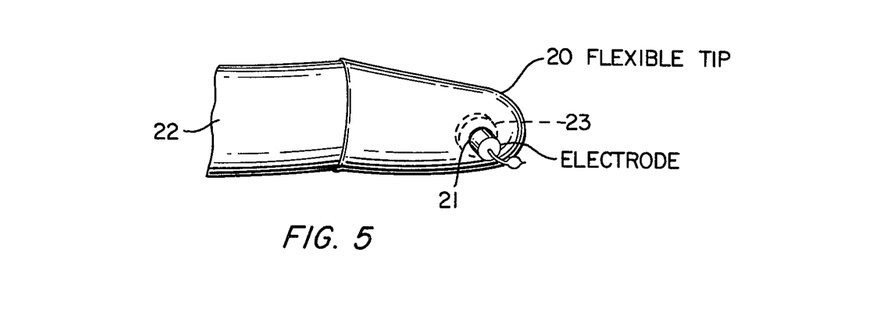
FIG. 5 illustrates in perspective view a second embodiment of applicator, in the form of a flexible fingertip arrangement.

Turning now to FIG. 5, illustrated therein is a second embodiment of applicator, taking the form of a finger-tip arrangement 20 of resilient material by which there is constituted on the one hand an alternate means of applying the tuberous pin electrode to say the fetal scalp and on the other hand additional feel of the situation is obtained. The applicator of FIG. 5 closely resembles a finger cot configuration and is to be worn over the end digit(s) of the finger 22 (most likely the index finger). Along the side of the flexible finger-tip applicator 20 there is provided at least one orifice or aperture 21 proximate the closed end thereof, which orifice(s) is substantially circular in shape and dimensioned to closely cooperate with that of the cylindrical base portion 1a of the electrode of say FIGS. 2A and 2B.

Such an applicator particularly provides the physician with good feel of the situation throughout the approach to the monitor target and application of the electrode. The electrode configuration depicted in FIG. 5 is that of FIG. 2A, including the concave structure of the top or back end of the base, which particularly permits the physician to exert a guidance of and force upon the electrode against the wall of the orifice of the finger-tip applicator to enable the electrode to be retained in the ready position while approaching the monitor site.

It is envisioned that the electrode may be assembled on the finger-tip applicator in such a way as to have the lead wires run along the interior of the applicator and along the index finger, then to be grasped, under tension if desired, between the thumb, palm and other fingers. Moreover, it is envisioned that this applicator may be loose enough on the finger to enable the easy extraction of the finger from the applicator, leaving the latter behind along with the electrode, particularly in the case of monitoring the unborn fetus. In this latter regard, it is pointed out that the particular embodiment of electrode employed may be that depicted in FIG. 1 (as demonstrated by the dashed line 23 in FIG. 5), in which the top portion 1b of the base 1 would, of course, securely maintain the electrode in and protruding from orifice 21.

Figure 6A:
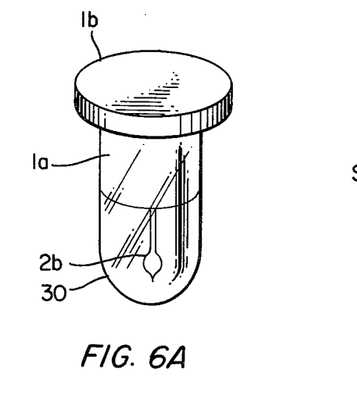
FIGS. 6A and 6B illustrate diagrammatically in side views the tuberous pin electrode of FIG. 1 in a sterile embodiment respectively prior to and at completion of application into a patient.
Figure 6B:
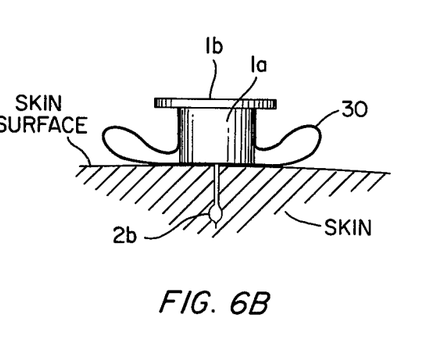

FIGS. 6A and 6B diagrammatically illustrate in side views the tuberous pin electrode of FIG. 1 in a sterile embodiment, respectively prior to and at the completion of application to the monitor site. Mounted on the cylindrical base portion 1a, e.g. secured by suitable adhesive, is a sterile covering or canopy 30 (here shown to be transparent for convenience sake) entirely enclosing the exposed portion of the active electrode element 2b. Canopy 30 may be made of any suitable material such as latex, which is light and flexible, i.e. readily deformable, and which can be relatively easily punctured by the active element 2b when force is exerted on the opposite end portion 1b of the electrode base at the time of application to the patient. By way of canopy 30, the sterility of the electrode is maintained until the very moment of insertion of the active electrode 2 into the patient occurs through the canopy. By pressing the electrode against the tissue and applying force, the cover and then the tissue is punctured thus providing protection from contamination of the tuberous pin element 2 until the actual puncturing of the skin at the desired site or target location.

It is to be noted particularly that each of the applicator embodiments, as well as the electrode embodiments, depicted herein are intended to be disposable arrangements.

Figure 7A:
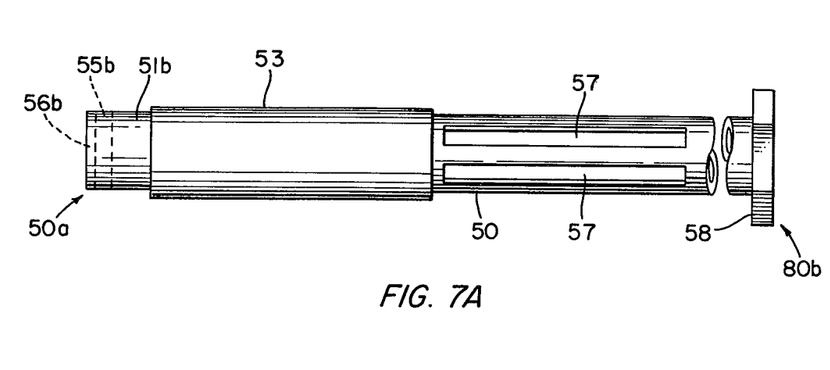
FIGS. 7A-7C illustrate respectively in bottom and left end and right end views another applicator embodiment, taking the form of a locking applicator arrangement.
Figure 7B:
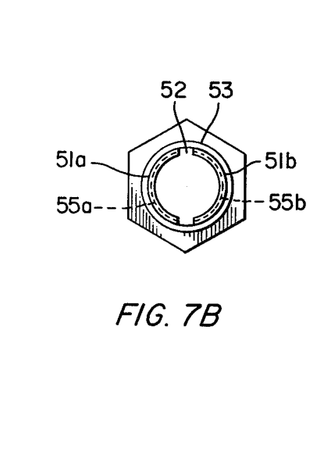
Figure 7C:
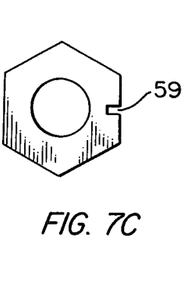
Figure 7D:
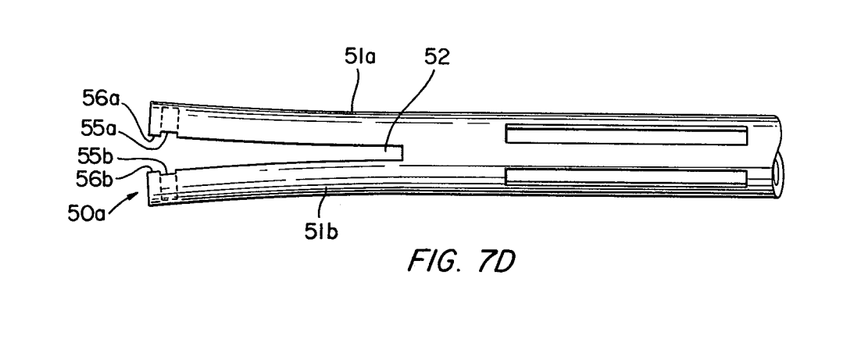
FIG. 7D is a sideview of the locking applicator of FIG. 7A with, however, the locking mechanism removed for clarity.

FIGS. 7A-7D illustrate another embodiment of electrode applicator, this time in the form of a locking applicator arrangement. FIGS. 7B and 7C respectively show the left end and right end views of the applicator of FIG. 7A, while FIG. 7D illustrates the main member of the applicator without the locking portion, and in the open or unlocked orientation.

The locking applicator of FIGS. 7A-7D is comprised of an elongated, cylindrically shaped main member 50, one end of which is divided into a pair of arms 51a and 51b which define a slot or channel 52 therebetween. Arranged on elongated main member 50 is a displaceable locking part 53, which is intended to interact with the operative, i.e. locking, end 50a of the applicator. Main member 50 and displaceable locking member 53 are composed of relatively rigid material such as polyethylene. Member 50 is constructed to have the arms 51a and 51b normally opening away from one another somewhat. Arms 51a and 51b have opposing recesses 55a, 55b in the surfaces thereof facing one another. Preferably, recesses 55a and 55b are substantially rectangular in shape (cross-section) for cooperating or mating with the base portion of the electrode to be received on the applicator for delivery to the patient. It is to be understood, however, that the actual shape of recesses 55a and 55b may take any suitable form, so long as they along with the rest of the operative portions of the arms 51a and 51b are shaped and dimensioned to cooperate with the intended base portion of the electrode.

Figures 8A, 8B, 9A, 9B, 9C:
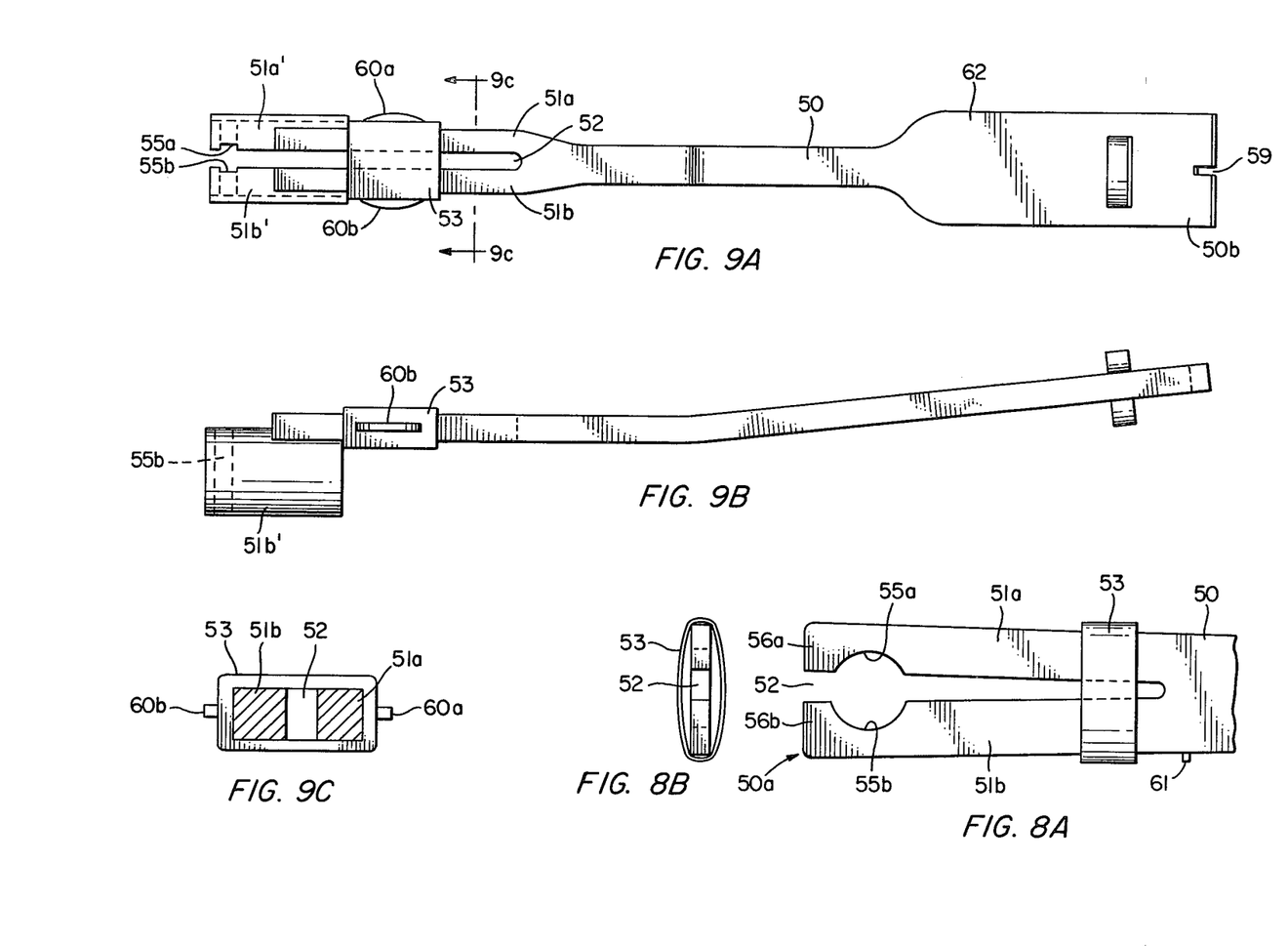
FIGS. 8A and 8B illustrate diagrammatically in side and end views respectively a version of the locking applicator of FIG. 7 having, however, a flat configuration.
FIGS. 9A and 9B illustrate in plan and side views respectively another version of the locking applicator of FIG. 7, having for the most part the flat configuration of the applicator of FIG. 8 with, however, the electrode receiving end having a cylindrical configuration.
FIG. 9C is a cross-section of the applicator of FIG. 9A taken along the line C—C.

As particularly illustrated in FIG. 7B, both elongated main member 50 and locking member 53 are cylindrical in configuration, although member 50 could instead have a flat configuration, such as is illustrated for example in FIGS. 8A and 8B. The applicator arrangement of FIGS. 7A-7B is particularly adapted for receiving the body structure illustrated in FIG. 2C. This electrode is received at the locking end of the applicator such that the cylindrical base portion of the former would be coaxial with main member 50. In this regard, the front tooth-like portions 56a, 56b, of the arms 51a, 51b engage the recess 1c of the base portion of the electrode of FIG. 2C.

The remainder of the elongated member 50 is provided with a series of elongated window openings 57, preferably four in number, which run parallel to the longitudinal axis of member 50, and also a hexagonally shaped distal or remote end piece 58. The window openings 57 serve on the one hand as shock absorbers, particularly in the case where an electrode of the type depicted in FIG. 2D is used, in which the window openings prevent excessive driving torque from being applied to the electrode. On the other hand, the window openings permit light from an endoscope to illuminate the presenting part of the patient, as will be particularly appreciated in connection with the monitoring of the unborn fetus through the cervix. The hexagonal shape of end piece 58 facilitates the generation of torque to be applied to the electrode, as needed, for application thereof to the patient. End piece 58 also is provided with a slot or recess 59 in which may be conveniently tucked the electrode lead(s) until disengagement is desired.

Although FIGS. 7A and 7B depict the locking member 53 in the form of a sliding cylindrical sleeve, which slides into its locking forward position to bias the arms 51a, 51b, together in a closely cooperating position, and slides back away from the locking end of the member 50 to its retracted position for enabling disengagement of the electrode from the applicator, it is to be understood that the relationship of locking member 53 and main member 50 may be such as to have the locking member rotatably threaded on the main member for rotation into and out of the locking position. It is to be noted further that member 50 is tubular and thus may provide an internal path for the leads to extend away from the locking end.

FIGS. 8A and 8B show a flat configuration of the locking applicator depicted in FIGS. 7A-7D, in which main member 50 and its locking end arms 51a, 51b have essentially a rectangular cross-section. Moreover, in this embodiment, the locking member 53 preferably takes on a substantially cross-sectional configuration. FIGS. 8A and 8B show locking member 53 in the retracted or unlocked position so as to define the full channel 52 between the arms 51a, 51b. As before, the applicator depicted in FIGS. 8A and 8B is particularly adapted for engagement with an electrode base such as that illustrated in FIG. 2C, only this time, due to the flat structure of the main member 50, the orientation of the electrode in the assembled position on the locking applicator is such as to have the operative end thereof facing perpendicular to the longitudinal direction of main member 50. In this regard, the thickness dimension of main member 50, in particular its associated arms 51a, 51b, is such as to cooperate with the width dimension of the recess 1c in the base portion of the electrode shown in FIG. 2C.

The locking applicator of FIGS. 8A and 8B operates in essentially the same manner as that of the applicator of FIGS. 7A-7D, wherein the electrode body is inserted between the arms 51a and 51b so as to engage the recesses 55a and 55b and teeth 56a and 56b accordingly. Therefollowing, the locking member 53 is moved longitudinally along main member 50 toward the locking end 50a, and thereby biasing the arms 51a and 51b toward one another and thus effecting the engagement with the intended electrode body portion. Because of the friction between the arms and the locking member, the latter maintains its position unless positively urged backward along the main member 50 towards the retracting position. FIG. 8A shows, moreover, a representative one of possibly a number of limit stops 61 by which it is intended that the locking member 53 be prevented from progressing too far along the shaft of main member 50 away from the locking and portion 50a.

FIGS. 9A-9C illustrate a further embodiment of the locking applicator, in which for the most part the main member 50 assumes a rectangular cross-sectional configuration except for the free-end portion of the locking arms 51a, 51b. The free-end portions of arms 51a, 51b assume instead a cylindrical configuration 51a', 51b'.

As is particularly illustrated in this embodiment, arms 51a, 51b are provided with respective locking ears 60a and 60b which are intended for engagement with locking member 53 to hold the latter securely in the locking position. In this instance, locking member 53 takes on a hollow rectangular configuration with a pair of slots on opposing sides thereof which are intended to cooperate with locking ears 60a, 60b. FIGS. 9A and 9B each illustrate the applicator in the locked mode where the electrode (not shown) is secured between the cylindrically shaped free ends of the arms 51a, 51b. Here again, the actual specific shape of the locking end portion of this applicator cooperates with the design of the rear portion of the electrode.

Main member 50 is provided with a flat paddle-shaped portion 62 at the end remote from the locking end portion, which serves the dual purposes of preventing locking member 53 from sliding off the shaft of main member 50 and also to present a pair of flat broad surfaces for easy grasping of the applicator by the physician, particularly in the event a certain amount of torque is desired in the application of the electrode to the patient. It is to be noted, moreover, particularly in FIG. 9B, that the shaft of main member 50 is bent substantially in the middle portion thereof to facilitate the approach to the patient, particularly in such difficult situations as the approach to the unborn fetus by way of the vagina and cervix. As before in the case of the locking applicator of FIG. 7D, a slot or recess 59 is provided in the end portion of 50b of main member 50 for convenient insertion of the electrode lead(s) while approaching the monitor site.

It is to be understood that it is within the scope of this invention for the locking applicator to also take the form of a tubular main member 50 with however the operative (locking) end portion thereof having a flat configuration similar to that of FIGS. 8A and 8B. In this regard the locking mechanism 53 may take either the tubular form depicted in FIG. 7A or the form of FIG. 9C, as desired.

There has been disclosed herein a disposable electrode for direct transcutaneous derivation of patient biopotentials, such as the ECG of an unborn fetus, the active electrode element of which has a tuberous pin configuration with at least one tuberosity arranged along its length for enabling atraumatic attachment to and removal from the patient. The active electrode element may be of curved and multi-tuberous configuration for particularly facilitating application and firm attachment thereof substantially parallel to the skin surface. Several embodiments of disposable applicator are disclosed by which the sense of feel of the effort of and during application is retained. These include a flexible member elongated for easy grasping by the hand and having one end thereof designed to cooperatively engage the electrode for stability yet permit the physician's finger to remain in contact with the electrode and a locking applicator arrangement which includes a displaceable locking piece enabling the electrode to firmly remain upon the applicator as the former is administered to the patient.

What is claimed is:

1. Self-holding electrode arrangement for direct transcutaneous derivation of biopotentials, such as the ECG of a fetus in fetal monitoring, comprising:
  (a) a base of electrically insulating material;
  (b) an active electrode element extending from said base, the extending portion thereof having along its length at least one tuberosity means for securely holding the electrode to the patient upon non-rotary insertion thereof;
  (c) a reference electrode element mounted to said base and spaced from said active electrode element; and
  (d) means for electrically connecting said active and reference electrode elements to a biopotential monitor.

2. Electrode arrangement according to claim 1 wherein said base has at least a first portion of substantially cylindrical shape and wherein said active electrode element projects outward from one end of said cylindrical first portion at least initially in a direction substantially parallel to the longitudinal direction of the latter.

3. Electrode arrangement according to claim 2 wherein said base has a disc-shaped second portion communication with the other end of said cylindrical first base portion, said disc-shaped second portion having a cross-sectional diameter greater than said first base portion.

4. Electrode arrangement according to claim 2 wherein said substantially cylindrically shaped first portion of said base has at least one transversely running recess.

5. Electrode arrangement according to claim 1 wherein said active electrode element is in a substantially straight pin-like configuration with a tuberosity proximate the free end thereof and having a substantially pointed free end.

6. Electrode arrangement according to claim 1 wherein said active electrode element is in a curved configuration with a tuberosity located proximate the free end thereof and having a substantially pointed free end.

7. Electrode arrangement according to claim 6 wherein the curved configuration of said active electrode element is such as to have its free end forming an angle of less than 180° with respect to the other end of the exposed portion thereof.

8. Electrode arrangement according to claim 1 wherein said active electrode element has a plurality of tuberosities of predetermined size relative to one another distributed along the length thereof.

9. Electrode arrangement according to claim 8 wherein said tuberosities are distributed substantially equidistant from one another.

10. Electrode arrangement according to claim 8 wherein said active electrode element has a plurality of tuberosities at least a predetermined one of which is of different size from the remainder.

11. Electrode arrangement according to claim 1 wherein said reference electrode element is a film of electrically conductive material covering a portion of the exterior of the base.

12. Electrode arrangement according to claim 11 wherein said base is substantially cylindrical in shape and said reference electrode element is in the form of a band of electrically conductive material arranged around the circumference of the base.

13. Electrode arrangement according to claim 1 wherein said base is substantially cylindrical in shape with said active electrode element projecting out one end thereof and with said reference electrode element covering at least a portion of the other end thereof.

14. Electrode arrangement according to claim 13 wherein said other end of the base is concave.

15. Electrode arrangement according to claim 1 further including a canopy secured to said base and covering said active electrode element, said canopy being composed of a readily deformable, perforatable material, forming a shield about said active electrode element, the arrangement of said canopy being such as to preserve the sterility of the active element up to the moment of actual application of the electrode arrangement to the monitor site.

16. Electrode arrangement according to claim 1 wherein said active electrode element has a curved configuration having a plurality of tuberosities located along the length thereof and a substantially pointed free end.

17. Electrode arrangement according to claim 16 wherein said tuberosities are predeterminably sized and spaced apart relative to one another.

18. Electrode arrangement according to claim 17 wherein the curved configuration of said active electrode element is such as to have its free end forming an angle of less than 180° with respect to the other end of the exposed portion thereof.

19. Electrode arrangement according to claim 1 wherein said active electrode element has a curved configuration and a substantially pointed free end.

20. In an electrode arrangement for direct transcutaneous derivation of patient biological parameters, such as the ECG of an unborn fetus, said electrode arrangement having a base of insulating material, spaced apart active and reference electrode elements on said base and means for electrically connecting said active and reference electrode elements to a bio-potential monitor, the improvement comprising the active electrode element having a tuberous pin configuration with at least one tuberosity means arranged along the length thereof for enabling the active electrode element of said electrode arrangement to be translationally inserted into the patient's epidermis and held substantially securely in place even upon subjection to external forces tending to dislodge said electrode arrangement and for enabling substantially atraumatic attachment and removal of the electrode arrangement to respectively from the patient.

21. Apparatus for use in monitoring biopotentials of an organism comprising:
(a) an elongated, flexible member at least one end of which has a fork-like configuration defining a channel which is predeterminably dimensioned;
(b) a holder removably slidably engaged in said channel;
(c) a self-retaining pin-like electrode element having at least one tuberosity along its length, extending from said holder and adapted to be relatively easily and atraumatically inserted into the epidermis of the organism by exerting a translational force upon said pin-like element via said member and holder; and
(d) means for electrically connecting said electrode element to a biopotential monitor.

22. In combination with an electrode arrangement for deriving at least one biological parameter of a patient such as a fetus, which electrode arrangement has a body member at least a portion of which has a predetermined configuration including relative to the main body portion thereof at least one projecting rear portion, a locking applicator arrangement comprising an elongated main member of relatively rigid material and having one end thereof longitudinally split to form a pair of opposed cooperating arms normally spaced apart to define a channel therebetween, each arm being predeterminably configured and having proximate the free end thereof and associated to the surface facing the opposing arm an opening mating with said projecting portion of said electrode arrangement body member to effect a secure locking of said electrode arrangement when said applicator assumes the locking orientation, and a displaceable locking part mounted on the main member at least proximate said one end thereof for movement toward respectively away from said one end in order to decrease respectively increase the dimension of said channel and thereby effect a locked respectively unlocked orientation, said one end of said main member cooperating with the predeterminably configured body member portion of the electrode arrangement to facilitate application thereof to the monitor site with the applicator in said locked orientation.

23. The combination of claim 22 wherein the body member of the electrode arrangement is composed of an electrically insulating material having a substantially cylindrical first portion with at least one transversely running groove therein.

24. The combination of claim 23 wherein the main elongated member of said locking applicator arrangement is substantially flat, and the cylindrical axis of the body member of said electrode arrangement is oriented substantially perpendicular to the longitudinal axis of said applicator arrangement when said electrode arrangement is locked onto said locking applicator arrangement.

25. The combination of claim 23 wherein the main member of said locking applicator arrangement is tubular, and the longitudinal axis of said electrode arrangement is oriented substantially parallel to the longitudinal axis of said applicator arrangement when said electrode arrangement is locked onto said locking applicator arrangement.

26. The combination of claim 22 further including at least one limit stop means arranged on the main member beyond the channel defined by said opposing arms and relatively remote from said split end for restricting the movement of said displaceable locking part away from said one end when assuming said unlocked orientation.

27. In combination with an electrode for deriving at least one biological parameter of a patient such as a fetus, which electrode has a body member at least a portion of which has a predetermined configuration including relative to the main body portion thereof at least one projecting rear portion of larger cross-sectional dimension, an active electrode element extending from said body member and means for electrically connecting said element to a bio-potential monitor, an applicator comprising an elongated substantially flat flexible member at least one end portion of which has a fork-like configuration having a pair of tine-like members defining a channel between the tine-like members which is predeterminably dimensioned and receives said predeterminably configured portion of the electrode body member at the main body portion thereof proximate said projecting rear portion, said applicator member being structured to be received in the palm of the hand and to extend along an extended finger thereof so as to enable the electrode to be securely maintained in contact with the free-end digit(s) of the extended finger(s) and the active electrode element to be translationally inserted into the patient.

* * * * *